(12) United States Patent
Chang et al.

(10) Patent No.: US 11,058,895 B2
(45) Date of Patent: Jul. 13, 2021

(54) COLLIMATOR AND MEDICAL ROBOT INCLUDING THE SAME

(71) Applicant: Daegu Gyeongbuk Institute of Science and Technology, Daegu (KR)

(72) Inventors: Pyung Hun Chang, Seoul (KR); Erkin Gezgin, Izmir (TR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 408 days.

(21) Appl. No.: 16/103,033

(22) Filed: Aug. 14, 2018

(65) Prior Publication Data

US 2019/0054317 A1    Feb. 21, 2019

Related U.S. Application Data

(60) Provisional application No. 62/545,983, filed on Aug. 15, 2017.

(51) Int. Cl.
| | |
|---|---|
| *G02B 27/30* | (2006.01) |
| *A61N 5/10* | (2006.01) |
| *A61B 34/30* | (2016.01) |
| *A61B 34/00* | (2016.01) |
| *A61B 34/20* | (2016.01) |

(52) U.S. Cl.
CPC ............ *A61N 5/1045* (2013.01); *A61B 34/30* (2016.02); *A61N 5/1067* (2013.01); *A61N 5/1083* (2013.01); *G02B 27/30* (2013.01); *A61B 34/20* (2016.02); *A61B 34/70* (2016.02); *A61N 5/1049* (2013.01); *A61N 2005/1094* (2013.01)

(58) Field of Classification Search
CPC .. A61N 5/1045; A61N 5/1083; A61N 5/1049; A61N 5/1067; A61B 34/70; A61B 34/30; G02B 27/30
See application file for complete search history.

(56) References Cited

U.S. PATENT DOCUMENTS

| | | | | |
|---|---|---|---|---|
| 4,450,578 | A * | 5/1984 | Hill | G21F 5/04 378/150 |
| 5,591,983 | A * | 1/1997 | Yao | G21F 5/04 250/505.1 |
| 5,654,996 | A * | 8/1997 | Steinberg | A61N 5/1042 378/150 |
| 5,757,881 | A * | 5/1998 | Hughes | A61N 5/1042 250/505.1 |
| 6,240,161 | B1 * | 5/2001 | Siochi | A61N 5/1042 378/65 |

(Continued)

*Primary Examiner* — David P Porta
*Assistant Examiner* — Djura Malevic
(74) *Attorney, Agent, or Firm* — Lex IP Meister, PLLC

(57) ABSTRACT

Provided is a collimator including a base unit configured to form a radiation path of light; a pair of first moving members rotatably installed in the base unit; a pair of second moving members movably installed in the base unit; and an actuator configured to externally receive power and transmit the power to the first moving members and the second moving members, wherein a first space may be formed between the first moving members, a second space may be formed between the second moving members, and the light may pass through a radiation area corresponding to an overlapping area of the first space and the second space.

14 Claims, 15 Drawing Sheets

(56) References Cited

U.S. PATENT DOCUMENTS

| | | | | |
|---|---|---|---|---|
| 6,266,393 B1 * | 7/2001 | Ein-Gal | A61N 5/1042 | 250/505.1 |
| 6,388,816 B2 * | 5/2002 | Brown | G21K 1/04 | 359/641 |
| 6,459,769 B1 * | 10/2002 | Cosman | A61N 5/1042 | 250/505.1 |
| 6,487,273 B1 * | 11/2002 | Takenaka | H01J 35/16 | 378/131 |
| 6,526,123 B2 * | 2/2003 | Ein-Gal | A61N 5/1042 | 250/505.1 |
| 6,621,891 B2 * | 9/2003 | Danielsson | G21K 1/04 | 378/149 |
| 6,730,924 B1 * | 5/2004 | Pastyr | A61N 5/1042 | 250/505.1 |
| 6,757,355 B1 * | 6/2004 | Siochi | A61N 5/1042 | 378/147 |
| 7,132,674 B2 * | 11/2006 | Pastyr | G21K 1/04 | 250/505.1 |
| 7,257,196 B2 * | 8/2007 | Brown | A61N 5/1042 | 378/150 |
| 7,783,007 B2 * | 8/2010 | Echner | G21K 1/04 | 378/65 |
| 7,893,412 B2 * | 2/2011 | Ein-Gal | A61N 5/1042 | 250/505.1 |
| 8,093,572 B2 * | 1/2012 | Kuduvalli | A61N 5/1042 | 250/505.1 |
| 8,213,569 B2 * | 7/2012 | Zaiki | A61B 6/08 | 378/16 |
| 8,637,841 B2 * | 1/2014 | Prince | A61N 5/1045 | 250/505.1 |
| 8,718,234 B2 * | 5/2014 | Echner | G21K 1/04 | 378/152 |
| 8,731,142 B2 * | 5/2014 | Tanabe | G21K 1/04 | 378/150 |
| 8,740,880 B2 * | 6/2014 | Pinault | A61N 5/1049 | 606/1 |
| 8,831,169 B2 * | 9/2014 | Zaiki | A61B 6/08 | 378/16 |
| 9,627,098 B2 * | 4/2017 | Ganguly | G21K 1/04 | |
| 10,071,263 B1 * | 9/2018 | Prince | A61N 5/1047 | |
| 10,071,265 B2 * | 9/2018 | Chang | A61B 6/0487 | |
| 10,500,416 B2 * | 12/2019 | Larkin | A61N 5/1045 | |
| 10,617,885 B2 * | 4/2020 | Flynn | A61N 5/1001 | |
| 10,765,383 B2 * | 9/2020 | Martens | A61B 6/06 | |
| 10,782,252 B2 * | 9/2020 | Gateshki | G01N 23/20008 | |
| 2005/0008121 A1 * | 1/2005 | Low | A61N 5/1027 | 378/65 |
| 2005/0063516 A1 * | 3/2005 | Kato | A61N 5/1042 | 378/152 |
| 2006/0067481 A1 * | 3/2006 | Morton | A61B 6/06 | 378/151 |
| 2008/0123813 A1 * | 5/2008 | Maurer | G21K 1/046 | 378/96 |
| 2008/0212737 A1 * | 9/2008 | D'Souza | A61N 5/1049 | 378/65 |
| 2009/0001295 A1 * | 1/2009 | Johnsen | G21K 1/046 | 250/505.1 |
| 2009/0074148 A1 * | 3/2009 | Echner | G21K 1/04 | 378/152 |
| 2009/0161827 A1 * | 6/2009 | Gertner | A61N 5/1017 | 378/65 |
| 2010/0016649 A1 * | 1/2010 | Prionas | A61N 5/1048 | 600/1 |
| 2010/0021378 A1 * | 1/2010 | Rousso | A61B 5/418 | 424/1.11 |
| 2010/0054408 A1 * | 3/2010 | Echner | A61N 5/1042 | 378/65 |
| 2011/0049395 A1 * | 3/2011 | Hashimoto | A61N 5/1045 | 250/505.1 |
| 2011/0066278 A1 * | 3/2011 | Pinault | A61N 5/1049 | 700/213 |
| 2012/0203490 A1 * | 8/2012 | Sayeh | A61N 5/1075 | 702/105 |
| 2013/0188779 A1 * | 7/2013 | Chao | A61B 8/085 | 378/150 |
| 2014/0239204 A1 * | 8/2014 | Orton | G21K 1/046 | 250/505.1 |
| 2015/0190658 A1 * | 7/2015 | Yu | A61N 5/10 | 600/1 |
| 2015/0283406 A1 * | 10/2015 | Chang | A61B 6/4429 | 378/65 |
| 2016/0325117 A1 * | 11/2016 | Arai | A61N 5/1048 | |
| 2016/0325118 A1 * | 11/2016 | Arai | A61N 5/1048 | |
| 2016/0361566 A1 * | 12/2016 | Larkin | A61N 5/1045 | |
| 2016/0361568 A1 * | 12/2016 | Chappelow | G06T 7/0012 | |
| 2017/0252579 A1 * | 9/2017 | Kilby | A61N 5/1075 | |
| 2017/0281972 A1 * | 10/2017 | Zhang | A61B 6/06 | |
| 2018/0021596 A1 * | 1/2018 | Arai | A61N 5/1045 | 600/1 |
| 2018/0200540 A1 * | 7/2018 | Flynn | A61N 5/1001 | |
| 2020/0016430 A1 * | 1/2020 | Yang | A61N 5/1045 | |

* cited by examiner

COLLIMATOR AND MEDICAL ROBOT INCLUDING THE SAME

CROSS-REFERENCE TO RELATED APPLICATION

This application claims the benefit of U.S. Provisional Application No. 62/545,983, filed on Aug. 15, 2017, in the United States Patent and Trademark Office, the disclosure of which is incorporated herein in its entirety by reference.

BACKGROUND

1. Field

One or more embodiments relate to a collimator and a medical robot including the same, and more particularly, to a collimator capable of precisely and quickly radiating light to a target and a medical robot including the collimator.

2. Description of the Related Art

A collimator controls an irradiation path of light emitted by a light source. In particular, in medical applications, a collimator is used to control the direction and scattering of radiation to precisely radiate a target such as a cancer cell of a patient.

Radiotherapy is a treatment that uses high-energy radiation to kill cancer cells. Radiation refers to the transmission of energy through a space or a material mediating the transmission. X-rays are a representative type of radiation.

Along with surgery and chemotherapy, radiotherapy is one of the three major cancer treatments. Radiotherapy requires hospitalization, takes only several minutes to 20 to 30 minutes each time, and does not cause pain during the treatment.

X-Knife (Radionics, USA), Novalis Tx (BrainLAB, Germany), Peacok (NOMOS Corp, USA), Trilogy (Varian Medical System, USA), and CyberKnife (Accuray Inc. USA) are radiotherapy systems. Most of these systems have been developed to reduce radiation errors and increase radiation accuracy during treatment based on a linear accelerator and an image guided radiotherapy (IGRT) technique.

Among these systems, the CyberKnife is a dedicated stereotactic radiotherapy system that has high precision. This system includes a compact linear accelerator mounted on a robotic arm with six joints, so that a target, such as a tumor, can be radiated from various directions.

As the CyberKnife tracks the coordinates of a gold marker implanted in a body by using body frame imaging based on a real-time image guiding technique, precise treatment is possible without use of a fixed invasive device. Unlike the Gamma Knife which can be used to treat only brain tumors, the CyberKnife enables whole-body cancer treatment and fractionation whereby treatment can be delivered several times instead of only once.

A collimator may be mounted on the CyberKnife to make radiation converge on a local area of a target. The collimator may spatially modulate the intensity of radiation to deliver enough radiation a tumor volume and minimize radiation exposure to normal cells.

According to the related art, a multileaf collimator (MLC) is used for spatial modulation of radiation intensity. The MLC includes two sets of leaves that face each other and radiation passes through a space formed between the leaves facing each other. Thus, other spaces in the MLC are shielded from the radiation.

At this time, a driving unit needs to be connected to each leaf to move it. As a result, the structure of the collimator is complex, and a space and weight required for the collimator in the CyberKnife increase.

In addition, 40 to 120 motors are required to move the leaves, and thus, the probability that one of the motors may malfunction increases. When even just one of the motors malfunctions, the whole system, and more specifically, the MLC, needs to be stopped, and therefore, treatment is interrupted.

SUMMARY

One or more embodiments include a collimator capable of precisely and quickly radiating light to a target and a medical robot including the collimator.

However, these embodiments are just examples and do not limit the scope of the present disclosure.

Additional aspects will be set forth in part in the description which follows and, in part, will be apparent from the description, or may be learned by practice of the presented embodiments.

According to one or more embodiments, a collimator includes a base unit configured to form a radiation path of light; a pair of first moving members rotatably installed in the base unit; a pair of second moving members movably installed in the base unit; and an actuator configured to externally receive power and transmit the power to the first moving members and the second moving members, wherein a first space may be formed between the first moving members, a second space may be formed between the second moving members, and the light may pass through a radiation area corresponding to an overlapping area of the first space and the second space.

The actuator may include a first actuation member installed at an end of each of the first moving members and configured to rotate each of the first moving members around a rotation shaft; and a second actuation member installed at an end of each of the second moving members and configured to move each of the second moving members along a motion shaft.

The second moving members may face each other with the second space formed therebetween and may be linearly moved along the motion shaft.

The second moving members may be rotatably installed in the base unit.

The first moving members and the second moving members may be each curved with a predetermined radius of curvature.

The pair of first moving members and the pair of the second moving members may be respectively positioned on concentric spheres.

Alternatively, the actuator may include a first actuation member installed at an end of each of the first moving members and configured to rotate each of the first moving members around a first rotation shaft; and a second actuation member installed at an end of each of the second moving members and configured to rotate each of the second moving members around a second rotation shaft.

According to one or more embodiments, a medical robot includes a link unit comprising a plurality of link members; a link driving unit configured to rotate the link members; and a collimator coupled to an end of the link unit and configured to contactlessly aim at a target, wherein the collimator may include a base unit configured to form a radiation path of light; a pair of first moving members rotatably installed in the base unit; a pair of second moving members movably installed in the base unit; and an actuator configured to externally receive power and transmit the power to the first moving members and the second moving members.

Rotation axes of the link driving unit may intersect each other at one point and may be formed respectively at ends of the link members.

The link members may include a first link and a second link connected to an end of the first link.

The first link and the second link may have each an arc shape and may be respectively positioned on concentric spheres of which a center is the intersection point.

The actuator may include a first actuation member installed at an end of each of the first moving members and configured to rotate each of the first moving members around a rotation shaft; and a second actuation member installed at an end of each of the second moving members and configured to move each of the second moving members along a motion shaft.

The second moving members may face each other with the second space formed therebetween and may be linearly moved along the motion shaft.

Alternatively, the actuator may include a first actuation member installed at an end of each of the first moving members and configured to rotate each of the first moving members around a first rotation shaft; and a second actuation member installed at an end of each of the second moving members and configured to rotate each of the second moving members around a second rotation shaft.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
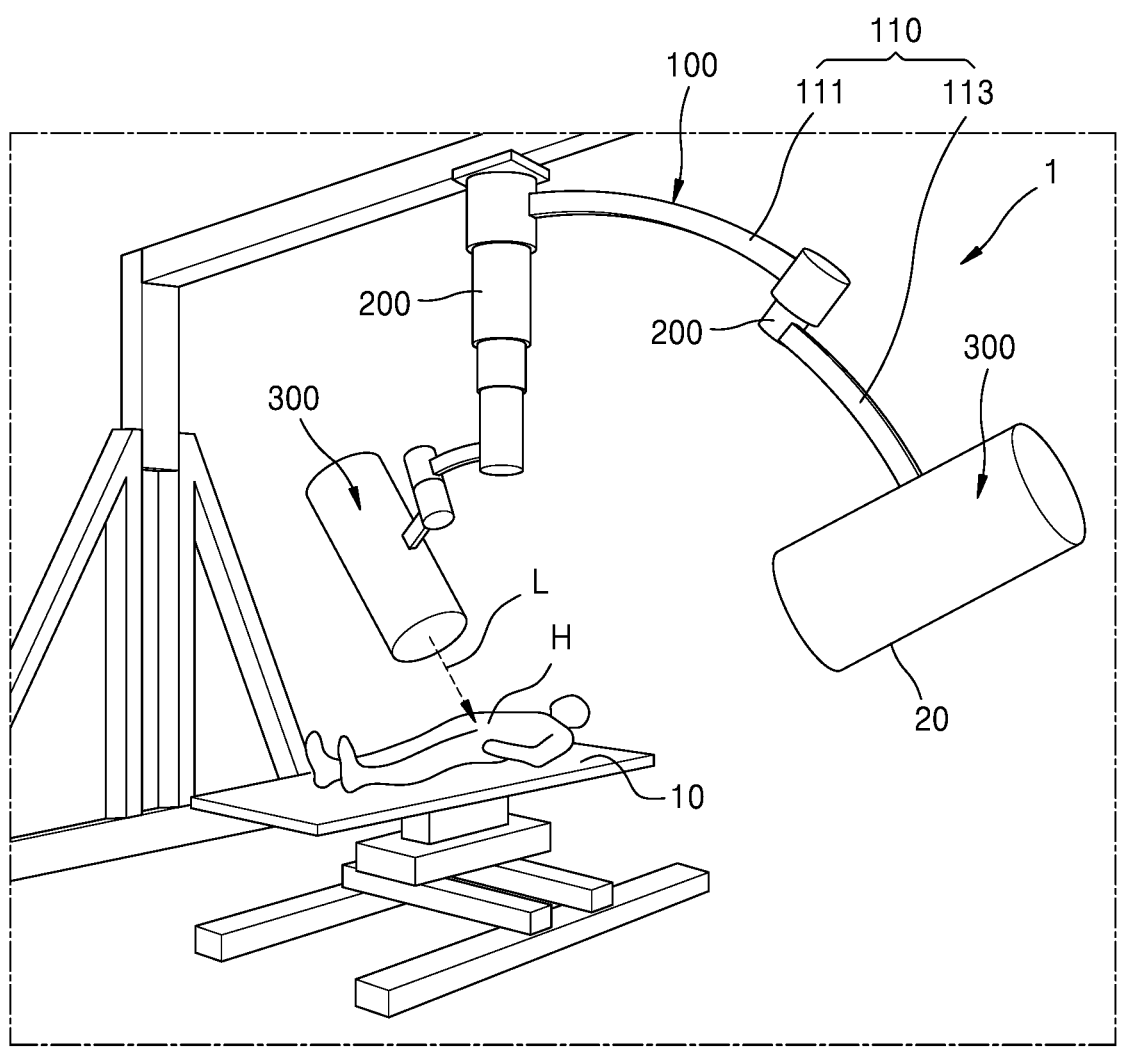
FIG. 1 is a perspective view of a medical robot according to an embodiment.

The present disclosure may include various modifications and different embodiments. In this regard, specific embodiments are illustrated in the drawings and will be described in detail. Advantageous effects, features, and methods for achieving the effects and features will become more apparent by explaining the embodiments in detail with reference to the accompanying drawings. However, the present disclosure is not limited to these embodiments but may be implemented in various modes.

The embodiments of the present disclosure will now be described in detail with reference to the accompanying drawings, in which like reference numerals denote like elements, and thus their description will be omitted.

It will be understood that when an element such as a layer, a film, a region, or a plate is referred to as being "on" another element, it can be directly on the other element, or intervening elements may also be present. In the drawings, the size of elements may be exaggerated or reduced for clarity. For instance, the size and thickness of each element may be arbitrarily illustrated in the drawings, and therefore, the present disclosure is not limited to the drawings.

In addition, the x, y, and z axes may not be limited to the three axes of a rectangular coordinates system but may be interpreted in a wider sense. For example, the x, y, and z axes may be orthogonal to one another or may indicate different directions which are not orthogonal.

Figure 2:
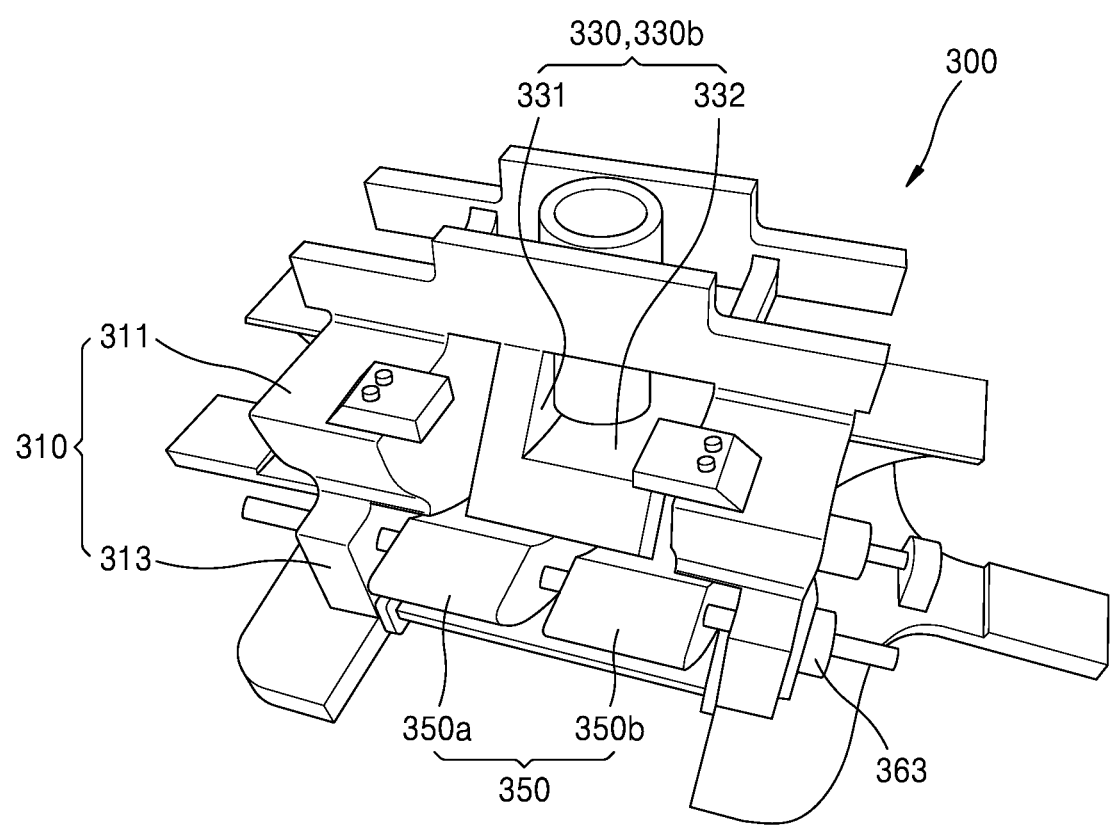
FIG. 2 is a perspective view of a collimator according to an embodiment.
Figure 3:
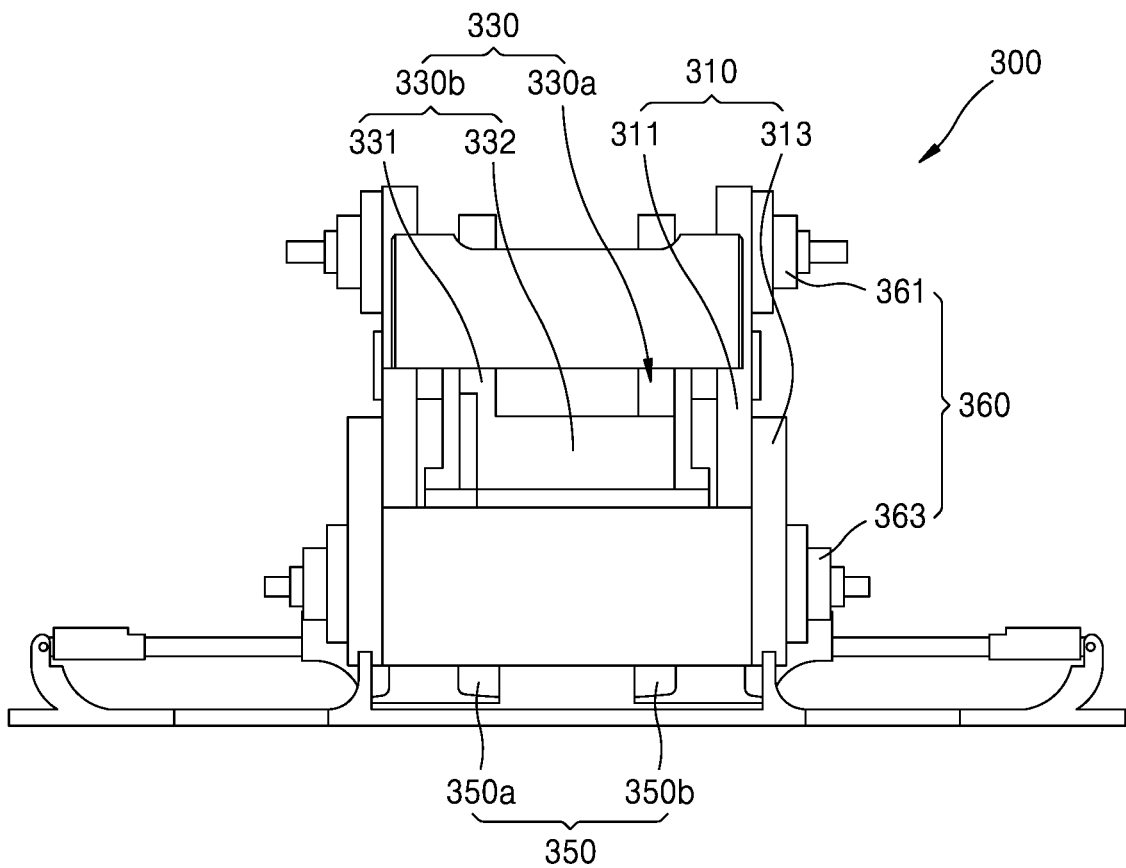
FIG. 3 is a front view of a collimator according to an embodiment.
Figure 4:
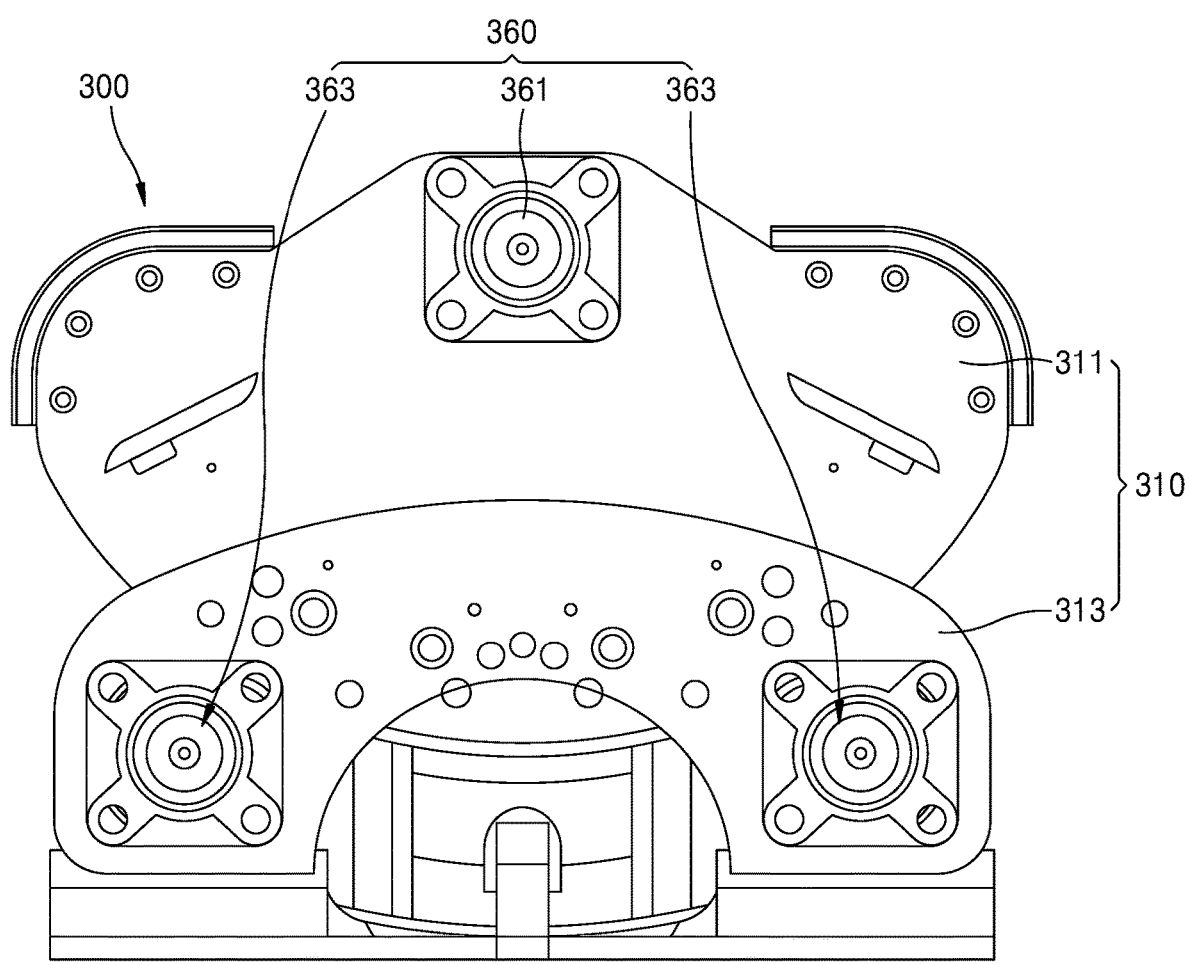
FIG. 4 is a side view of a collimator according to an embodiment.
Figure 5:
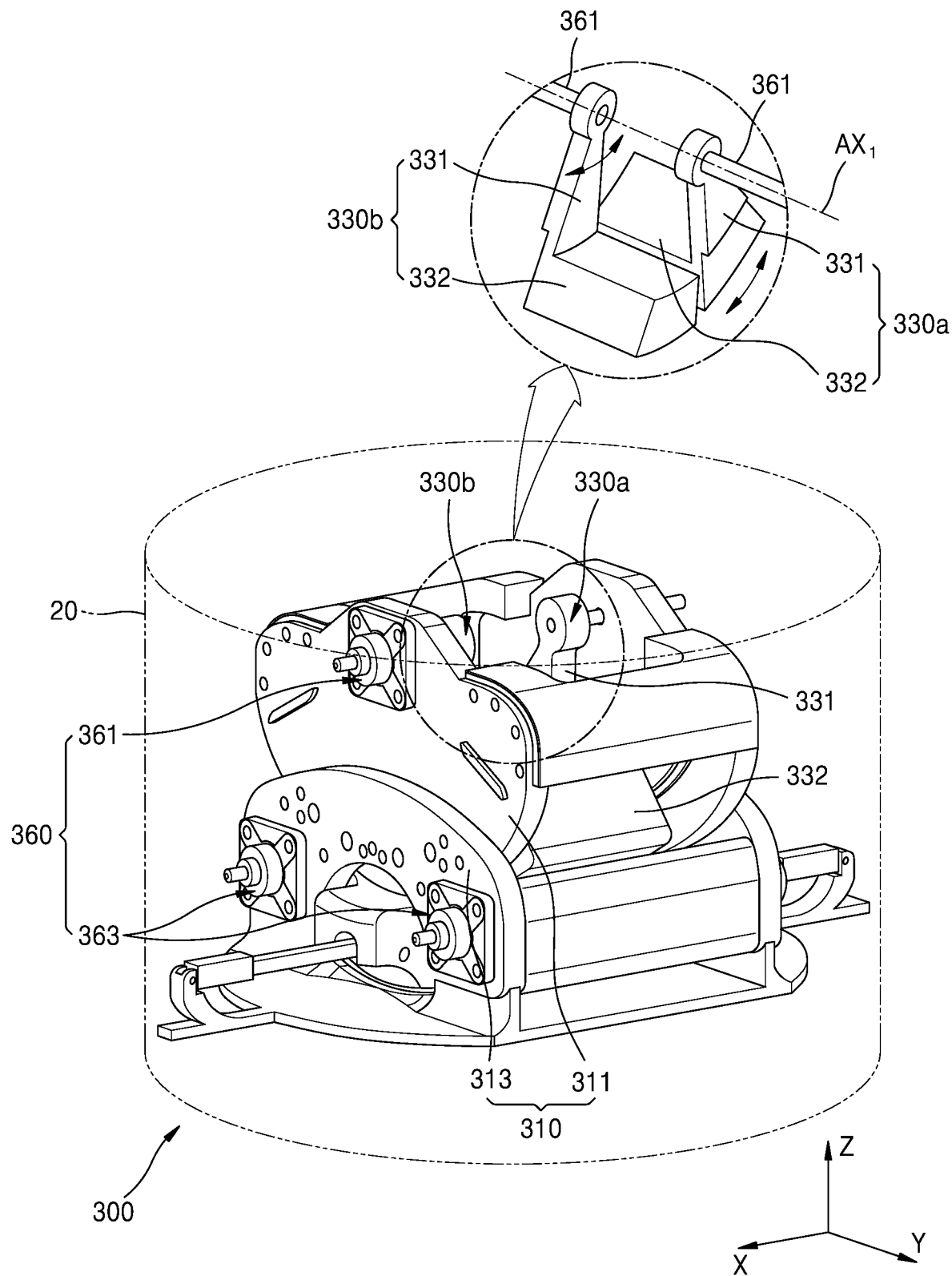
FIG. 5 is a perspective view of a collimator according to an embodiment.
Figure 6:
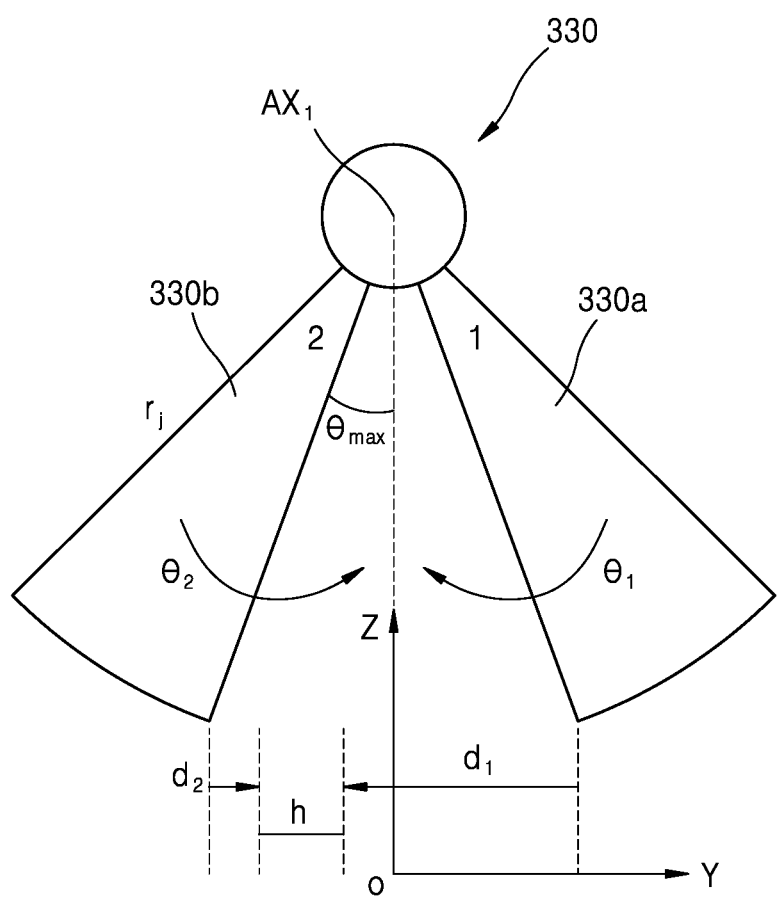
FIGS. 6 and 7 are conceptual diagrams showing the principle of operation of a collimator, according to an embodiment.
Figure 7:
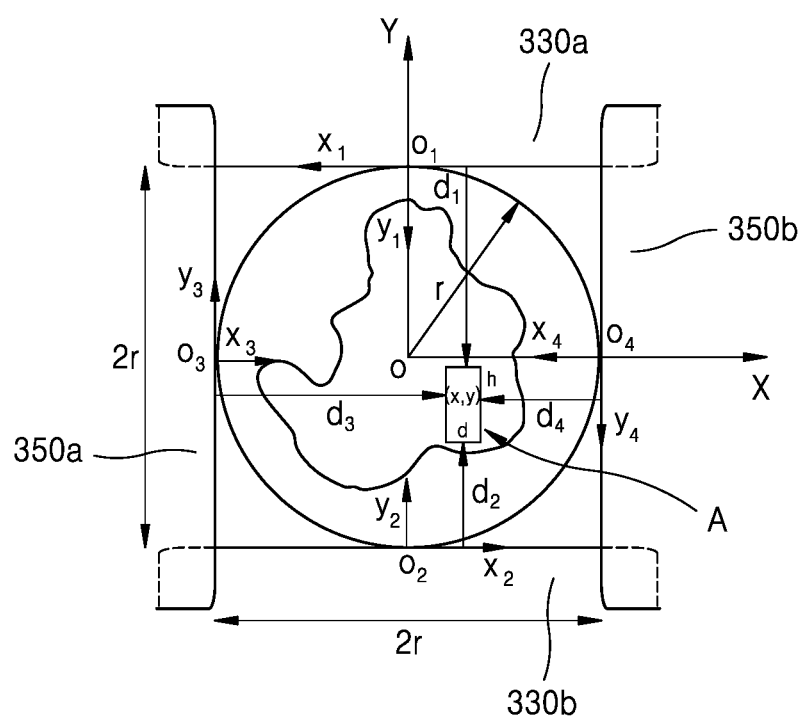
Figure 8:
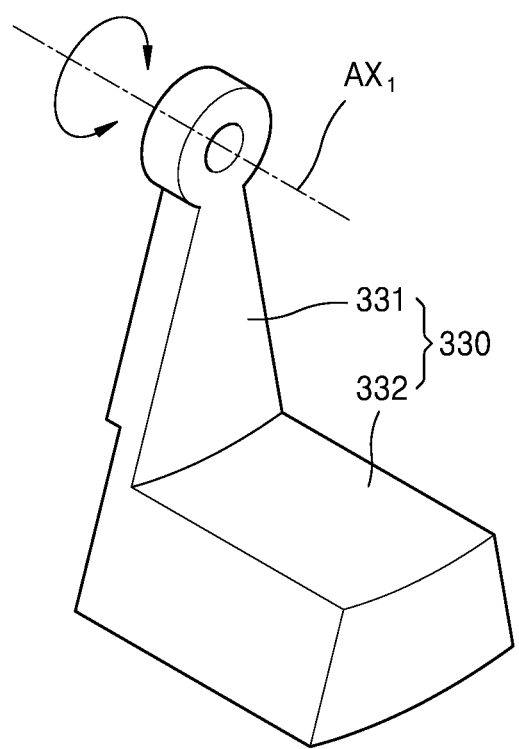
FIG. 8 is a perspective view of a first moving member according to an embodiment.

FIG. 1 is a perspective view of a medical robot according to an embodiment. FIG. 2 is a perspective view of a collimator according to an embodiment. FIG. 3 is a front view of a collimator according to an embodiment. FIG. 4 is a side view of a collimator according to an embodiment. FIG. 5 is a perspective view of a collimator according to an embodiment. FIGS. 6 and 7 are conceptual diagrams showing the principle of operation of a collimator, according to an embodiment. FIG. 8 is a perspective view of a first moving member according to an embodiment. FIGS. 11A through 11D are bottom views illustrating various irradiation ranges set by a collimator, according to embodiments.

Referring to FIGS. 1 through 5 and FIG. 8, a collimator 300 may include a base unit 310, a first moving member 330, a second moving member 350, and an actuator 360.

FIG. 1 shows a medical robot 1 including the collimator 300, according to an embodiment. The collimator 300 may be coupled to an end of a link unit of the medical robot 1, which will be described below. The collimator 300 may contactlessly aim at a target H, e.g., a patient.

In an embodiment, the target H may be a patient, and more specifically, an affected area, such as a tumor, in the patient's body. The patient may be positioned on a bed 10.

The collimator 300 is an optical device that controls the direction and scattering of light L. In detail, the collimator 300 may minimize a radiation dose rate in an area other than the target H by controlling the direction and scattering of radiation during radiotherapy.

In an embodiment, the collimator 300 is used in the medical robot 1 for radiotherapy or the like and adjusts a radiation path. However, the present disclosure is not limited to these embodiments. The collimator 300 may be variously modified so as to be used, for example, in an optical device such as a camera.

Referring to FIGS. 1 through 5 and FIG. 9, the radiation path of the light L may be formed in the base unit 310. The base unit 310 may close portions except for a space formed by the first and second moving members 330 and 350, which will be described below.

A portion of the base unit 310 may be connected to a light source (not shown) and receive the light L from the light source. In detail, the light L may be generated in the medical robot 1 and provided to the base unit 310. The light L may move inside the base unit 310 and may reach the target H after passing through an overlapping portion of a first space and a second space. The first space is formed between a pair of first moving members 330a and 330b, and the second space is formed between a pair of second moving members 350a and 350b.

Referring to FIGS. 1 and 5, the base unit 310 may be positioned inside a hollow cylinder 20. Accordingly, compared to a case when the collimator 300, and more specifically, the base unit 310, is installed in a member having a cuboid or square pillar shape, a space occupied by and weight of the base unit 310 may be reduced.

Referring to FIGS. 3 through 5, the first moving member 330 and the second moving member 350 may be movably coupled to the base unit 310. The base unit 310 may include a first base 311 and a second base 313.

FIG. 4 is a side view of the collimator 300 according to an embodiment. The first base 311 may be coupled to the second base 313. The first moving member 330 may be coupled to the first base 311, and the second moving member 350 may be coupled to the second base 313.

Referring to FIG. 4, a first actuation member 361, which transmits power to the first moving member 330, may be installed in the first base 311. A second actuation member 363, which transmits power to the second moving member 350, may be installed in the second base 313.

The first base 311 and the second base 313 may overlap each other and positions thereof may be fixed via a fastening member, e.g., a bolt, placed in the overlapping portion thereof such that the first and second bases 311 and 313 do not move with respect to each other. A pair of the first bases 311 and a pair of the second bases 313 may be provided. The first bases 311 may face each other and the second bases 313 may face each other.

Accordingly, the first moving member 330 and the second moving member 350 may be positioned among the first bases 311 and the second bases 313 to be movable. The first moving member 330 receives power from the actuator 360, and more specifically, from the first actuation member 361. The second moving member 350 receives power from the actuator 360, and more specifically, from the second actuation member 363.

The first base 311 and the second base 313 may include a material which blocks penetration of the light L, e.g., radiation.

Accordingly, the light L, which has been emitted from the light source and then received in the base unit 310, is prevented from escaping through other areas than a radiation area, which is formed by the first moving member 330 and the second moving member 350.

Referring to FIG. 4, the first base 311 and the second base 313 are separately formed and coupled to each other using a fastening member in the collimator 300 in an embodiment, but the present disclosure is not limited thereto. The first base 311 and the second base 313 may be integrally formed or modified in other various ways.

Referring to FIGS. 2, 5, 6, and 8, the first moving member 330 may be rotatably installed in the base unit 310. A pair of the first moving members 330a and 330b may be provided. The first moving member 330 may include a moving body 331 and a shielding portion 332.

Referring to FIG. 8, a first rotation shaft $AX_1$ may be formed at an end of the moving body 331. The moving body 331 may extend from the first rotation shaft $AX_1$ in a radial direction.

The shielding portion 332 may be connected to an opposite end of the moving body 331 and positioned in a path of the light L, and more specifically, a radiation path. The opposite end of the moving body 331 faces the end at which the first rotation shaft $AX_1$ is formed.

Like the base unit 310, the shielding portion 332 may be formed using a material which blocks penetration of radiation. Referring to FIG. 5, the shielding portion 332 may allow the light L to pass through the first space formed between the first moving members 330a and 330b facing each other.

Referring to FIG. 8, the shielding portion 332 may be curved with a predetermined radius of curvature.

Accordingly, the radiation area A (see FIG. 7) of the light L onto the target H may be variously positioned on a sphere formed by the rotation of the first moving members 330a and 330b, as compared to the case when the shielding portion 332 is flat.

Referring to FIG. 5, the first moving members 330a and 330b may be positioned to face each other and rotated in a clockwise or counterclockwise direction around the first rotation shaft $AX_1$, which is shared by the first moving members 330a and 330b.

The first moving members 330a and 330b may be independently rotated in the same direction or opposite directions.

In an embodiment, when the first moving member 330a is rotated in the clockwise direction, the first moving member 330b may be rotated in either the clockwise direction or the counterclockwise direction. When the first moving member 330a is rotated in the counterclockwise direction, the first moving member 330b may be rotated in either the clockwise direction or the counterclockwise direction.

Each of the first moving members 330a and 330b may be rotated by power from the actuator 360, and more specifically, the first actuation member 361. A rotation angle of each of the first moving members 330a and 330b may be determined by the first actuation member 361.

When the first moving members 330a and 330b are rotated in the same direction, the area of the first space, i.e., a gap between the first moving members 330a and 330b, may be widened or narrowed according to a difference in a rotation speed between the first moving members 330a and 330b.

When the first moving members 330a and 330b are rotated in opposite directions, and more specifically, when the first moving members 330a and 330b are rotated toward each other, the area of the first space may be rapidly narrowed. Also, when the first moving members 330a and 330b are rotated away from each other, the area of the first space may be rapidly widened.

Referring to FIGS. 2, 3, and 7-, the second moving member 350 may be movably installed in the base unit 310. At this time, a pair of the second moving members 350a and 350b may be provided.

In detail, the second moving member 350 may be linearly moved to the right and the left (based on FIG. 3) along a motion shaft.

Like the base unit 310, the second moving member 350 may include a material which blocks penetration of radiation. Referring to FIG. 2, the light L may be allowed to pass through the second space formed between the second moving members 350a and 350b facing each other.

Referring to FIG. 2, the second moving members 350a and 350b may be positioned to face each other and moved in a left-and-right direction along the motion shaft, which is shared by the second moving members 350a and 350b.

In an embodiment, the second moving member 350 may be linearly moved along the motion shaft, and the second space may be formed between the second moving members 350a and 350b facing each other.

Although the second moving members 350a and 350b are linearly moved, the present disclosure is not limited thereto. The second moving member 350 may be rotatably installed like the first moving member 330 or modified in various ways in one or more embodiments.

The second moving members 350a and 350b may be independently moved in the same direction or in opposite directions.

In an embodiment, when the second moving member 350a is moved to the left (based on FIG. 2), the second moving member 350b may be moved in the same direction, i.e., to the left, or in an opposite direction, i.e., to the right. When the second moving member 350a is moved to the right (based on FIG. 2), the second moving member 350b may be moved in the same direction, i.e., to the right, or in an opposite direction, i.e., to the left.

Referring to FIG. 2, each of the second moving members 350a and 350b may be moved by power from the actuator 360, and more specifically, the second actuation member 363. A moving distance of each of the second moving members 350a and 350b may be determined by the second actuation member 363.

When the second moving members 350a and 350b are moved in the same direction, the area of the second space, i.e., a gap between the second moving members 350a and 350b, may be widened or narrowed according to a difference in a moving speed between the second moving members 350a and 350b.

When the second moving members 350a and 350b are moved in opposite directions, and more specifically, when the second moving members 350a and 350b are moved toward each other, the area of the second space may be rapidly narrowed; and when the second moving members 350a and 350b are moved away from each other, the area of the second space may be rapidly widened. The light L may be generated in the light source and flows into the base unit 310. The first moving members 330a and 330b and the second moving members 350a and 350b may be positioned in a traveling path of the light L. An overlapping portion of the first space, which is formed between the first moving members 330a and 330b, and the second space, which is formed between the second moving members 350a and 350b, may be defined as the radiation area A. The light L may be radiated to the target H through the radiation area A.

In an embodiment, the actuator 360 may externally receive power and transmit the power to the first moving member 330 and the second moving member 350. The actuator 360 may include the first actuation member 361 and the second actuation member 363.

The first actuation member 361 and the second actuation member 363 may be separately provided. The first actuation member 361 may transmit the power to the first moving members 330a and 330b such that the first moving members 330a and 330b may be rotatable in the base unit 310 around the first rotation shaft $AX_1$ of the first moving members 330a and 330b, and more specifically, the moving body 331. The second actuation member 363 may transmit the power to the second moving members 350a and 350b such that the second moving members 350a and 350b may linearly move along the motion shaft.

In an embodiment, a plurality of first actuation members 361 may be provided and may independently transmit the power to the first moving members 330a and 330b, respectively.

Accordingly, the first moving members 330a and 330b may be independently rotated in the same direction, e.g., the clockwise or counterclockwise direction, or in opposite directions, respectively.

When the first moving members 330a and 330b are rotated in the same direction, i.e., the clockwise or counterclockwise direction, the rotation speed of each of the first moving members 330a and 330b may be changed to widen or narrow the area of the first space between the first moving members 330a and 330b.

The first actuation member 361 may be coupled to the base unit 310, and more specifically, the first base 311. A plurality of first actuation members 361 may be provided and respectively coupled to the pair of first bases 311 facing each other.

Referring to FIGS. 5 and 6, the pair of first moving members 330a and 330b, which receive the power from the first actuation member 361, may be independently rotated around the first rotation shaft $AX_1$.

Accordingly, the first space may be formed between the first moving members 330a and 330b, and more specifically, a pair of shielding portions 332 facing each other. The light L may be passed through only the first space.

In an embodiment, a plurality of second actuation members 363 may be provided and may independently transmit the power to the second moving members 350a and 350b, respectively.

Accordingly, the second moving members 350a and 350b may be independently moved in the same direction, e.g., to the left or to the right (based on FIG. 2), or in opposite directions, respectively.

When the second moving members 350a and 350b are moved in the same direction, i.e., to the left or to the right, the moving speed of each of the second moving members 350a and 350b may be changed to widen or narrow the area of the second space between the second moving members 350a and 350b.

The second actuation member 363 may be coupled to the base unit 310, and more specifically, the second base 313. A plurality of second actuation members 363 may be provided and respectively coupled to the pair of second bases 313 facing each other.

Referring to FIGS. 2, 5, and 7, the pair of second moving members 350a and 350b, which receive the power from the second actuation member 363, may be independently moved along the motion shaft. Accordingly, the second space may be formed between the second moving members 350a and 350b, and the light L may be passed through only the second space.

Referring to FIGS. 11A through 11D, the first moving members 330a and 330b may be moved by power from the first actuation member 361 and the second moving members 350a and 350b may be moved by power from the second actuation member 363. The light L, e.g., radiation, may passed through the radiation area A, i.e., an overlapping area of the first space between the pair of first moving members 330a and 330b and the second space between the pair of second moving members 350a and 350b.

As the first moving members 330a and 330b and the second moving members 350a and 350b are moved, various radiation areas $A_1$, $A_2$, $A_3$, and $A_4$ may be formed as the radiation area A, as shown in FIGS. 11A through 11D.

Accordingly, the collimator 300 may radiate the light L to the target H through the radiation area A. As compared to a multileaf collimator (MLC), in which actuators as many as shielding members transmit power to the respective shielding members, each of the shielding members linearly moves, and the light L is passed through a space formed between shielding members facing each other, the collimator 300 may form the radiation area A by transmitting power to the pair of first moving members 330a and 330b and the pair of second moving members 350a and 350b using relatively fewer actuators, i.e., at most four actuation members 361 and 363.

In addition, the structure of the collimator 300 may be simplified due to the pair of first moving members 330a and 330b and the pair of second moving members 350a and 350b, and the light L may be quickly and precisely radiated to the target H since the light L is passed through the radiation area A, i.e., the overlapping area of the first space between the first moving members 330a and 330b and the second space between the second moving members 350a and 350b.

Kinematic analysis of the collimator 300 will be described in detail below.

Referring to FIGS. 6 and 7, to set the positions of the pair of first moving members 330a and 330b facing each other, rotation angles $\theta_1$ and $\theta_2$ of the respective first moving members 330a and 330b need to be set. The rotation angles $\theta_1$ and $\theta_2$ may be obtained using moving distances $d_1$ and $d_2$ from ends of the respective first moving members 330a and 330b to the radiation area A in a Y-axis direction (based on FIG. 6), which are defined as Equations 1:

$$d_1 = r - r_j \operatorname{Sin}(\theta_{max} - \theta_1)$$

$$d_2 = r - r_j \operatorname{Sin}(\theta_{max} - \theta_2) \quad (1)$$

wherein "r" is a radius of a circle having, as a diameter, a maximum distance between the first moving members 330a and 330b in an XY plane (based on FIGS. 5 and 7), the maximum distance being the same as a maximum distance between the second moving members 350a and 350b, and "$r_j$" is a radius of rotation of the first moving member 330.

When a position of the target H is fixed, the moving distances $d_1$ and $d_2$ of the respective first moving members 330a and 330b may be determined. A controller (not shown) may receive information on the moving distances $d_1$ and $d_2$ and calculate the rotation angles $\theta_1$ and $\theta_2$ of the respective first moving members 330a and 330b using Equations 2:

$$\theta_1 = \theta_{max} - \operatorname{Sin}^{-1}\left(\frac{r - d_1}{r_j}\right) \quad (2)$$

$$\theta_2 = \theta_{max} - \operatorname{Sin}^{-1}\left(\frac{r - d_2}{r_j}\right).$$

Referring to FIG. 7, when the position of the target H is fixed in the XY plane (based on FIGS. 5 and 7) and the radiation area A is set, the moving distances $d_1$ and $d_2$ of the respective first moving members 330a and 330b and moving distances $d_3$ and $d_4$ of the respective second moving members 350a and 350b may be defined, based on information about the radiation area A, as Equations 3:

$$d_1 = r - \left(y + \frac{h}{2}\right), d_2 = r + \left(y - \frac{h}{2}\right), d_3 = r + \left(x - \frac{d}{2}\right), \quad (3)$$

$$d_4 = r - \left(x + \frac{d}{2}\right).$$

At this time, the radiation area A is located at a point (x, y) with a center among the first moving members 330a and 330b and the second moving members 350a and 350b as an origin of the XY plane (based on FIGS. 5 and 7) and has a width "d" in an X-axis direction and a width of "h" in the Y-axis direction.

When the moving distances $d_1$ and $d_2$ defined as Equations 3 are applied to Equations 2, the rotation angles $\theta_1$ and $\theta_2$ of the respective first moving members 330a and 330b and the moving distances $d_3$ and $d_4$ of the respective second moving members 350a and 350b may be finally defined as:

$$\theta_1 = \theta_{max} - \operatorname{Sin}^{-1}\left(\frac{y + \frac{h}{2}}{r_j}\right),$$

$$\theta_2 = \theta_{max} - \operatorname{Sin}^{-1}\left(\frac{\frac{h}{2} - y}{r_j}\right),$$

$$d_3 = r + \left(x - \frac{d}{2}\right), d_4 = r - \left(x + \frac{d}{2}\right).$$

Accordingly, when the position of the target H is fixed and simple information, such as a central value (x, y), the width "d" in the X-axis direction, and the width of "h" in the Y-axis direction of the radiation area A in the XY plane (based on FIGS. 5 and 7), is obtained, the rotation angles $\theta_1$ and $\theta_2$ of the respective first moving members 330a and 330b and the moving distances $d_3$ and $d_4$ of the respective second moving members 350a and 350b may be calculated, so that an operating mechanism is simplified and easy control is accomplished.

Figure 9:
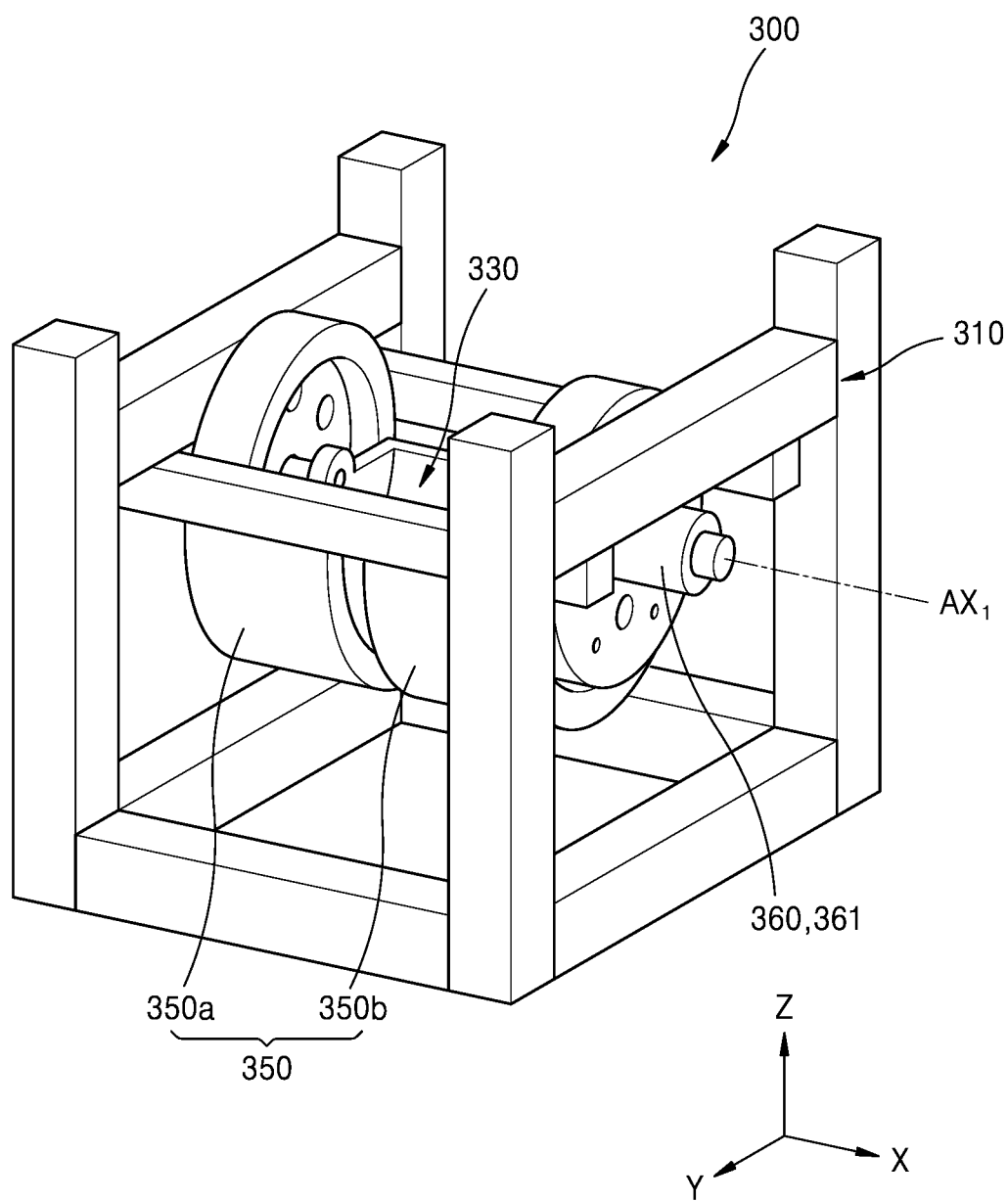
FIG. 9 is a perspective view of a collimator according to one or more embodiments.

A collimator according to one or more embodiments will be described below. FIG. 9 is a perspective view of a collimator according to one or more embodiments.

Referring to FIG. 9, the collimator 300 may include the base unit 310, the first moving member 330, the second moving member 350, and the actuator 360.

A pair of second moving members 350, i.e., the second moving members 350a and 350b, may be provided. The second moving members 350a and 350b may be movably installed in the base unit 310. The second moving members 350a and 350b may be linearly moved along a motion shaft, which is an X-axis (based on FIG. 9). The second moving members 350a and 350b may be curved with a predetermined radius of curvature.

As compared to when the second moving members 350a and 350b are flat, a radiation path of the light L may be expanded to a three-dimensional domain and a radiation area of the light L may be variously formed in a limited space.

The collimator 300 of FIG. 9 is the same as the collimator 300 described above with reference to FIGS. 2 through 8 and FIGS. 11A through 11D, excepting that the second moving members 350a and 350b are curved with the predetermined radius of curvature. Thus, redundant descriptions will be omitted.

Figure 10:
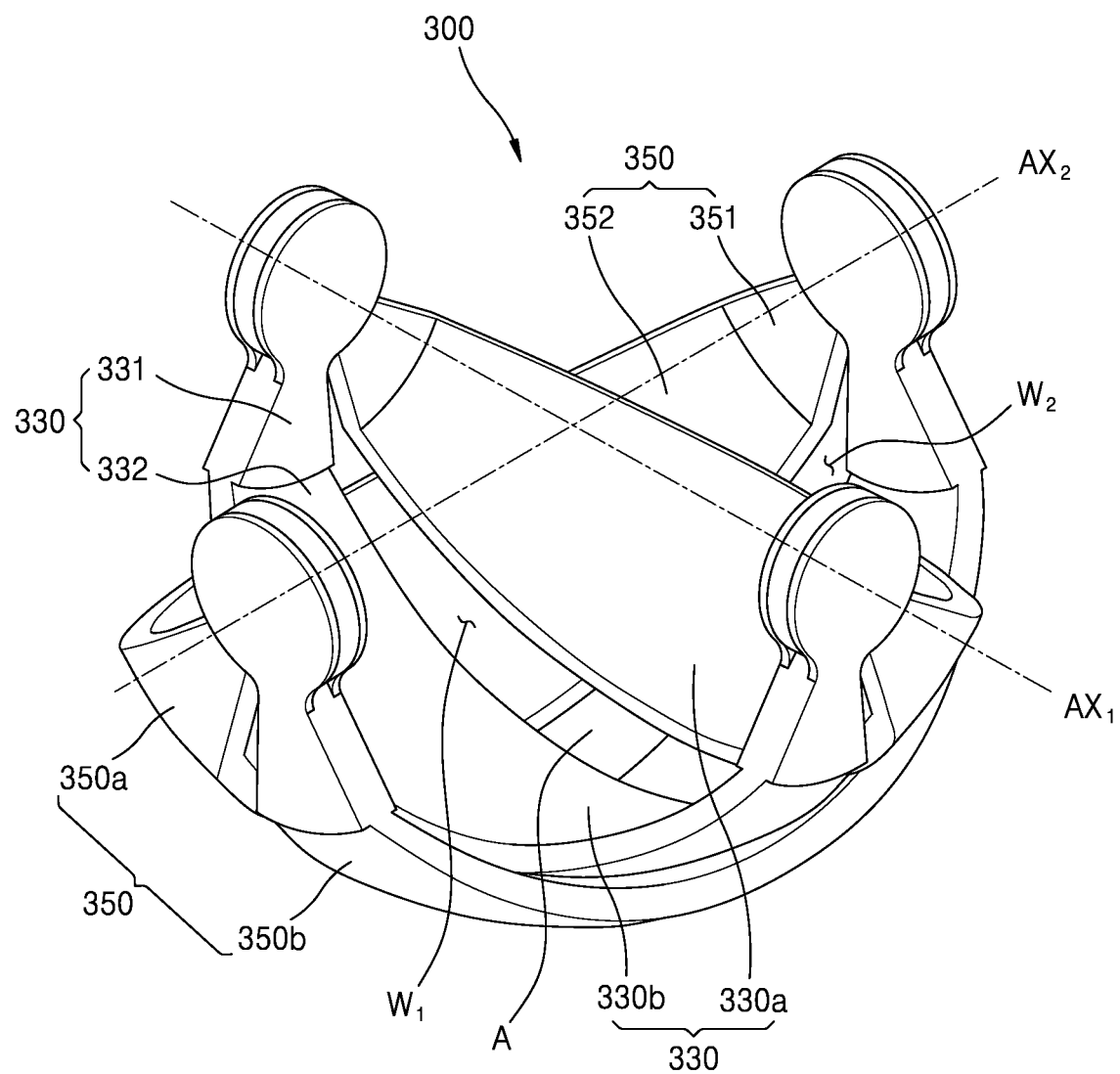
FIG. 10 is a schematic diagram of a collimator according to one or more embodiments.
Figure 11A:
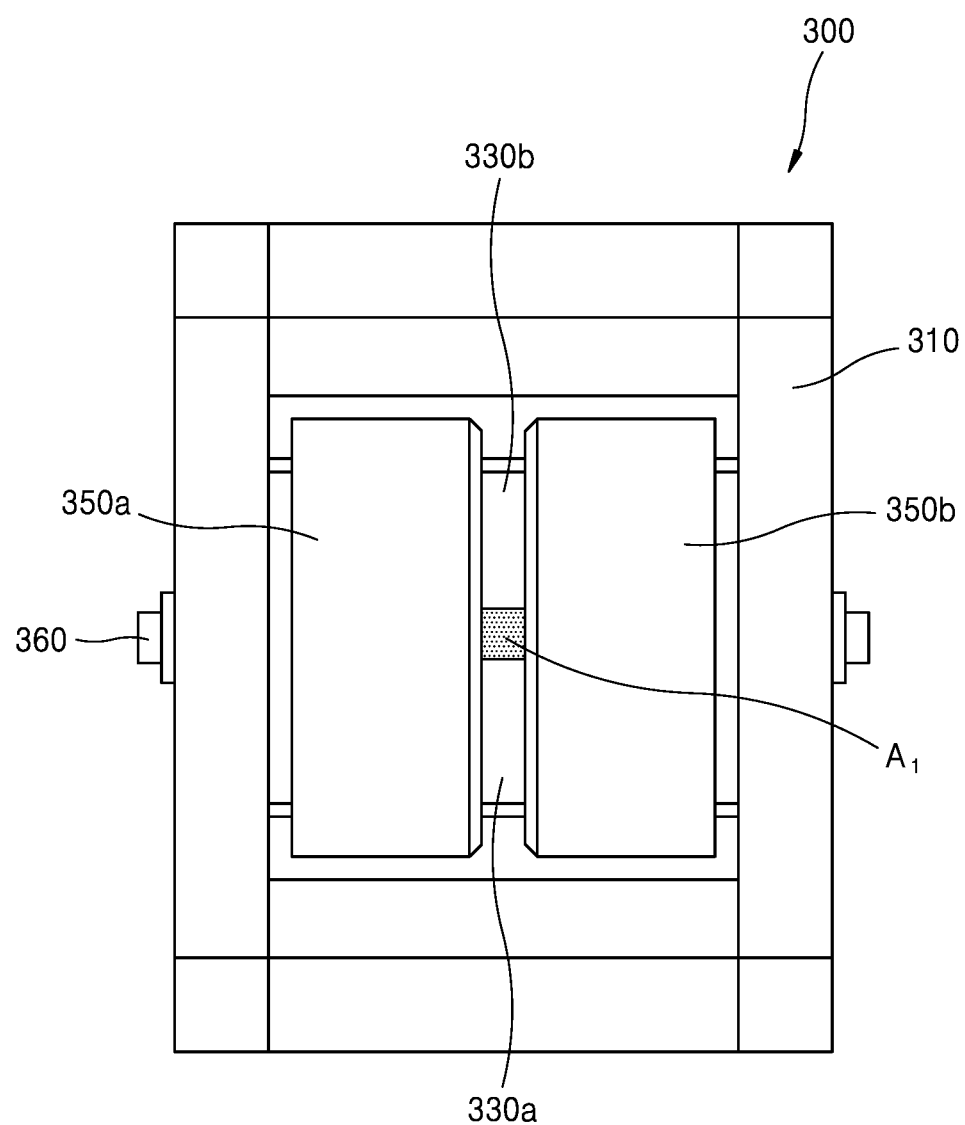
FIGS. 11A through 11D are bottom views illustrating various irradiation ranges set by a collimator, according to embodiments.
Figure 11B:
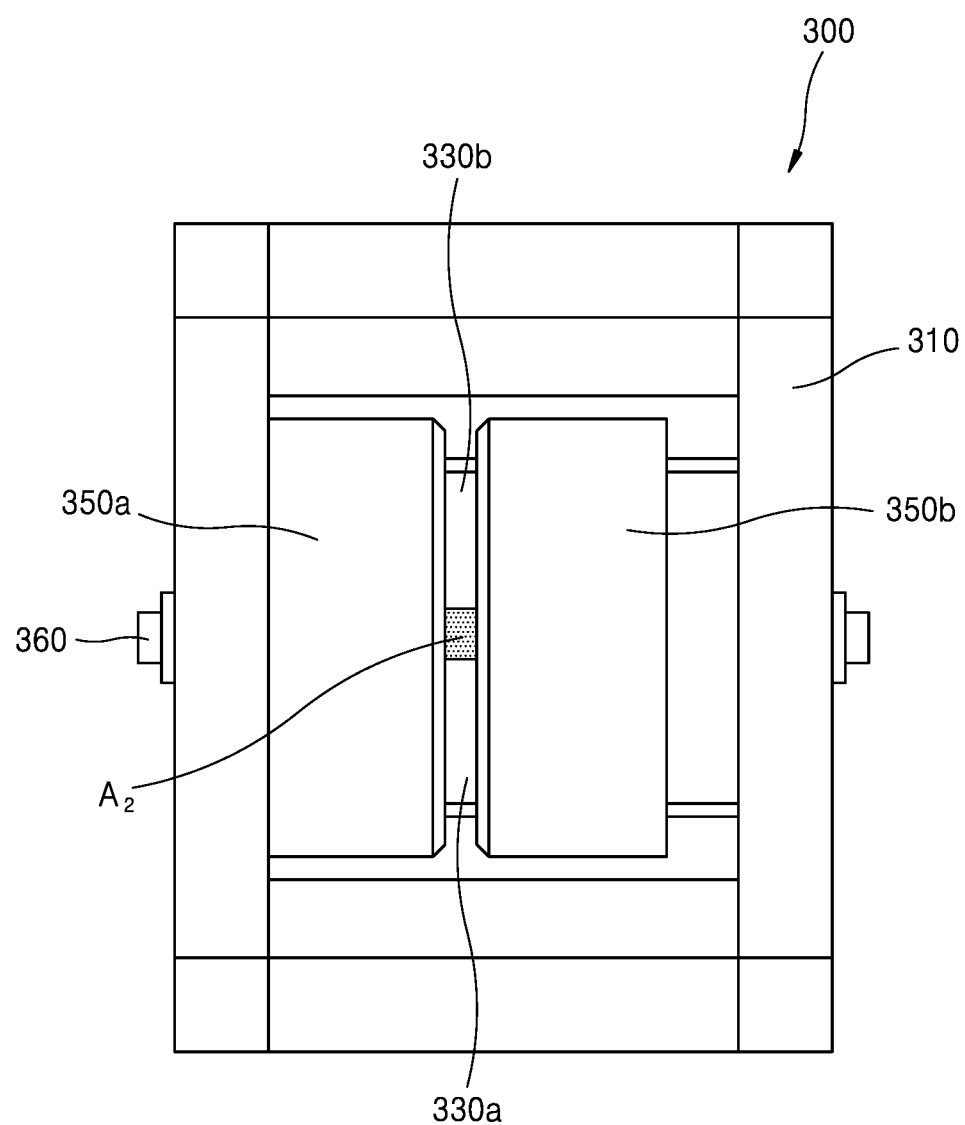
Figure 11C:
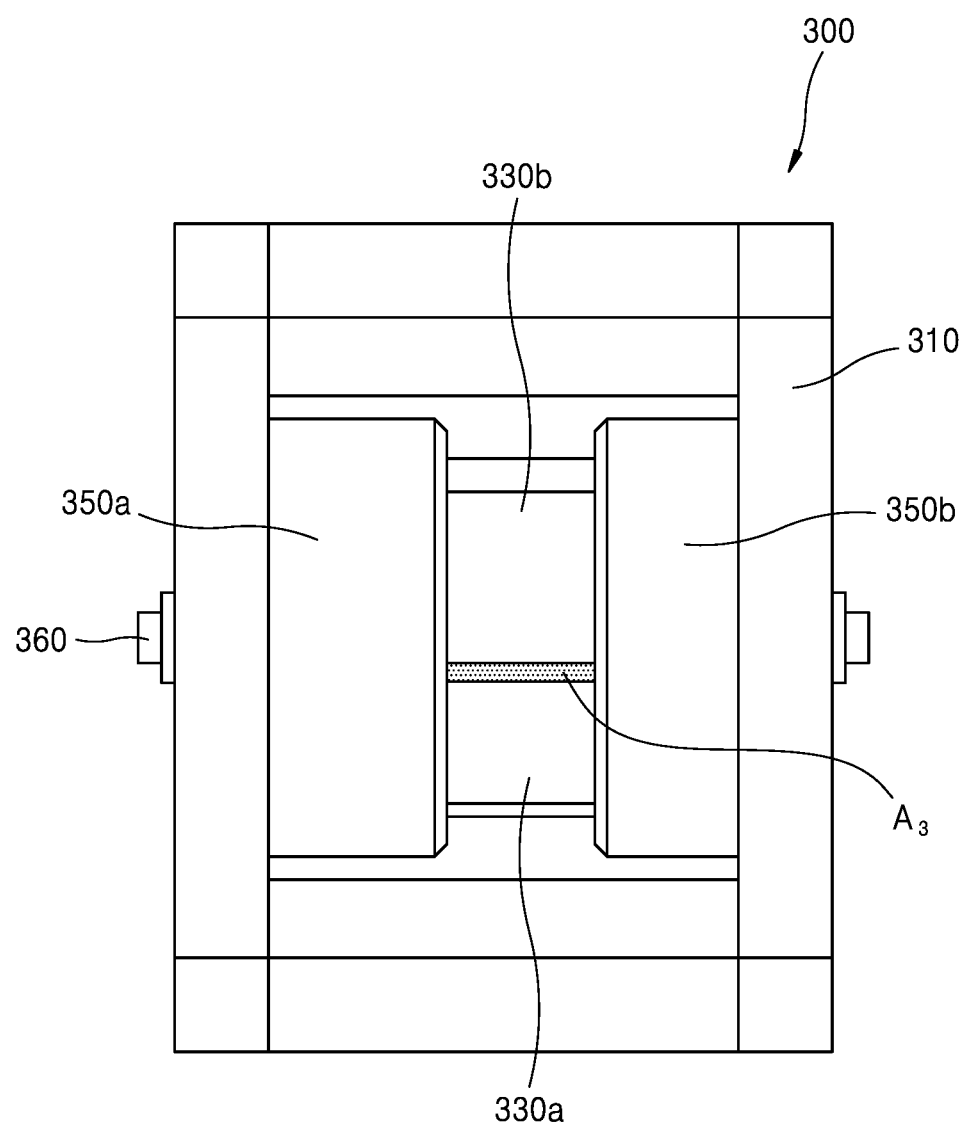
Figure 11D:
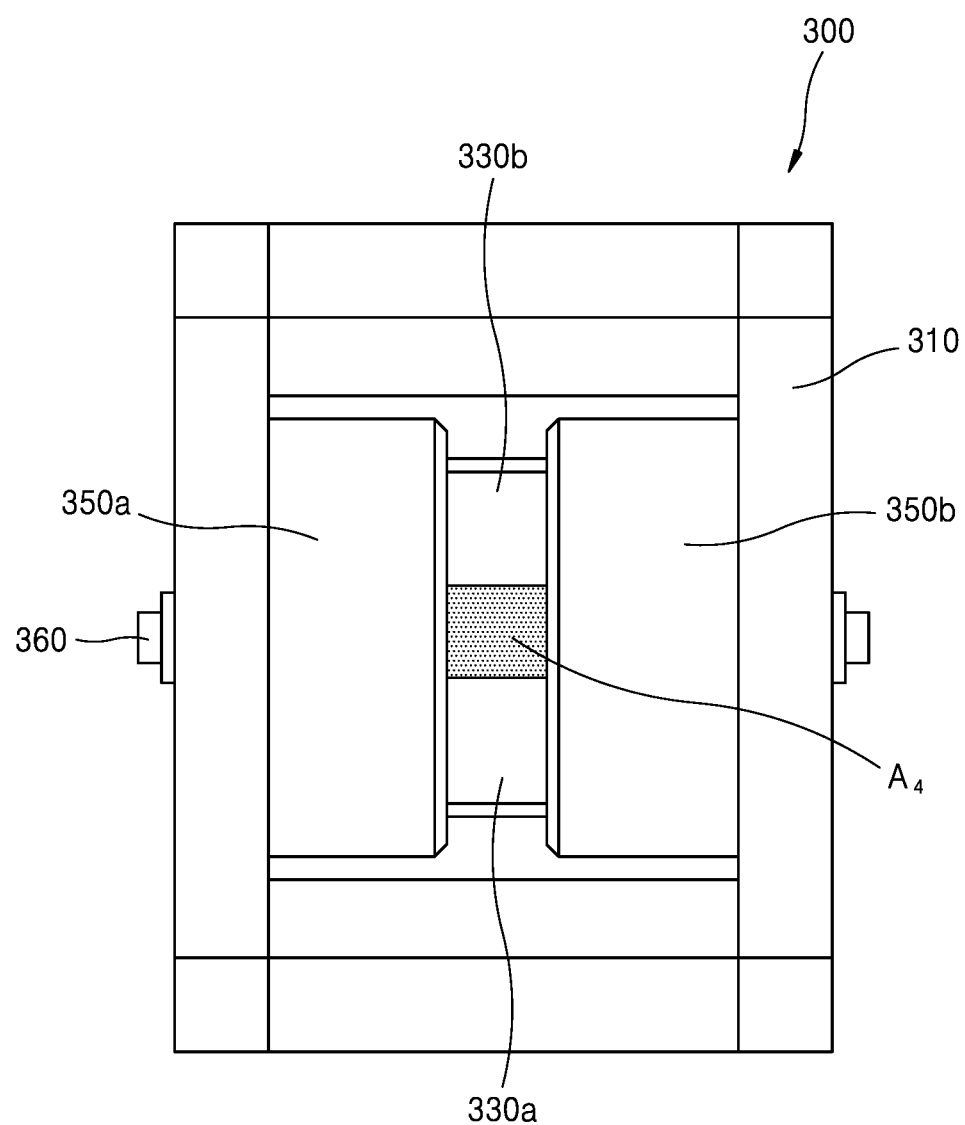

A collimator according to one or more embodiments will be described below. FIG. 10 is a schematic diagram of a collimator according to one or more embodiments.

Referring to FIG. 10, the collimator 300 may include the base unit 310, the first moving member 330, the second moving member 350, and an actuator.

A pair of second moving members 350, i.e., the second moving members 350a and 350b, may be provided. The second moving members 350a and 350b may be rotatably installed in the base unit 310. The second moving members 350a and 350b may be curved with a predetermined radius of curvature and may be rotated around a second rotation shaft $AX_2$ in the clockwise or counterclockwise direction.

Referring to FIG. 10, like the first moving member 330 of FIG. 8, each of the second moving members 350a and 350b may include a moving body 351 and a shielding portion 352.

The second moving members 350a and 350b are rotated around the second rotation shaft $AX_2$. The second moving members 350a and 350b may have the same shape as the first moving members 330a and 330b. In detail, the second rotation shaft $AX_2$ may be formed at an end of the moving body 351, and the moving body 351 may extend from the second rotation shaft $AX_2$ in a radial direction.

The shielding portion 352 may be connected to an opposite end of the moving body 351 and positioned in a path of the light L, and more specifically, a radiation path. The opposite end of the moving body 351 faces the end at which the second rotation shaft $AX_2$ is formed. Like the base unit 310, the shielding portion 352 may be formed using a material which blocks penetration of the light L.

The light L may be passed through a second space $W_2$ formed between the second moving members 350a and 350b facing each other. In detail, the radiation area A may be formed in an overlapping area of a first space $W_1$ between the first moving members 330a and 330b and the second space $W_2$ between the second moving members 350a and 350b, and the light L, e.g., radiation, may be radiated through only the radiation area A to an outside where the target H is positioned.

The shielding portion 352 may be curved with a predetermined radius of curvature. Accordingly, the radiation area A of the light L onto the target H may be variously positioned on a sphere formed by the rotation of the second moving members 350a and 350b, as compared to when the shielding portion 352 is flat.

Referring to FIG. 10, the second moving members 350a and 350b may be positioned to face each other and rotated in the clockwise or counterclockwise direction around the second rotation shaft $AX_2$, which is shared by the second moving members 350a and 350b.

The second moving members 350a and 350b may be rotated in the same direction or opposite directions.

For example, when the second moving member 350a is rotated in the clockwise direction, the second moving member 350b may be rotated in the clockwise direction. When the second moving member 350a is rotated in the counterclockwise direction, the second moving member 350b may be rotated in the counterclockwise direction.

Each of the second moving members 350a and 350b may be rotated by power from the actuator, and more specifically, a second actuation member. A rotation angle of each of the second moving members 350a and 350b may be determined by the second actuation member.

Unlike the second moving member 350 linearly moved by power from a linear accelerator in the previous embodiment described above, the second moving member 350 is rotated around the second rotation shaft $AX_2$ in the clockwise or counterclockwise direction in the current embodiment.

When the second moving members 350a and 350b are rotated in the same direction, the area of the second space $W_2$, i.e., a gap between the second moving members 350a and 350b, may be widened or narrowed according to a difference in a rotation speed between the second moving members 350a and 350b.

When the second moving members 350a and 350b are rotated in opposite directions, the area of the second space $W_2$ between the second moving members 350a and 350b may be narrowed.

The structures and operating principles of the base unit 310, the first moving member 330, and the actuator 360 of the collimator 300 according to the current embodiment are the same as those according to previous embodiments described above, excepting that the second moving members 350a and 350b are rotated around the second rotation shaft $AX_2$ like the first moving members 330a and 330b. Thus, redundant descriptions will be omitted.

Hereinafter, the structures, operating principles, and effects of a medical robot according to an embodiment will be described below.

Figure 12:
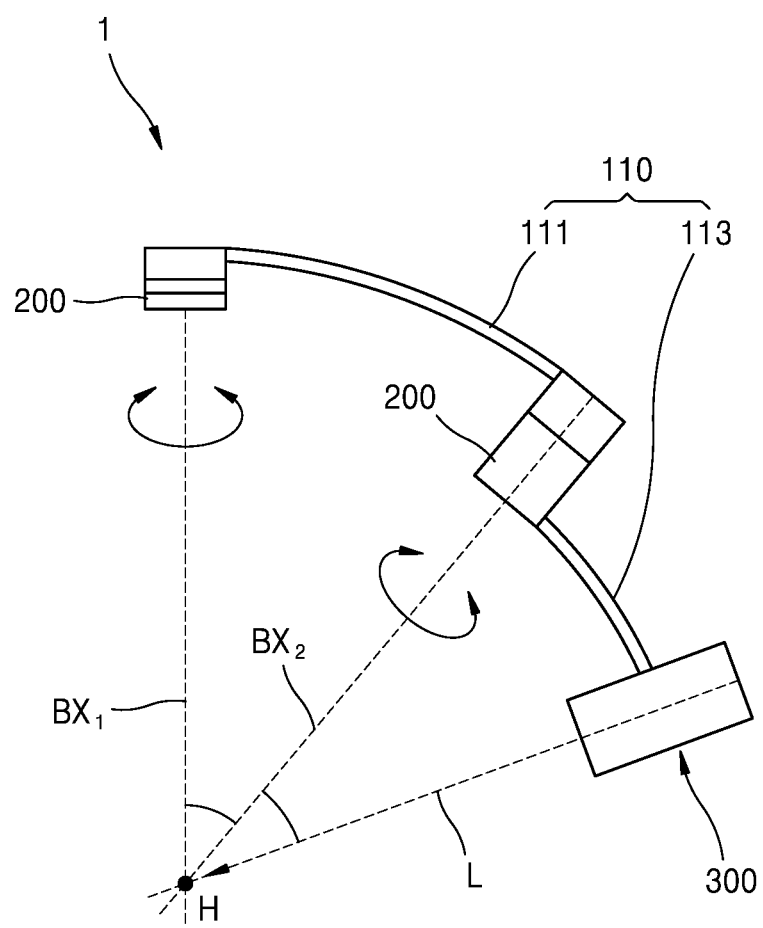
FIG. 12 is a diagram of a state in which rotation axes intersect at one point in a medical robot, according to an embodiment.

FIG. 1 is a perspective view of a medical robot according to an embodiment. FIG. 12 is a diagram of a state in which rotation axes intersect at one point in a medical robot, according to an embodiment.

Referring to FIGS. 1 and 12, the medical robot 1 may include a link unit 100, a link driving unit 200, and the collimator 300.

The link unit 100 may include a plurality of link members 110, and more specifically, a first link 111 and a second link 113.

The first link 111 and the second link 113 may have an arc shape and may be respectively positioned on concentric spheres of which the center is an intersection of a first link driving axis $BX_1$ and a second link driving axis $BX_2$. The target H is positioned at the intersection.

A distance from the first link 111 to the center may be greater than a distance from the second link 113 to the center, so that the first link 111 and the second link 113 are prevented from interfering with each other when the second link 113 is rotated around the second link driving axis $BX_2$.

Referring to FIGS. 1 and 12, the link driving unit 200 may rotate the link members 110. In detail, the link driving unit 200 may transmit power to the first link 111 to rotate the first link 111 around the first link driving axis $BX_1$ and transmit power to the second link 113 to rotate the second link 113 around the second link driving axis $BX_2$.

Referring to FIG. 12, a plurality of link driving units 200 may be provided. One of the link driving units 200 may be coupled to an end of the first link 111 and another one of the link driving units 200 may be provided in a portion where the second link 113 is connected to the first link 111.

Accordingly, the first link 111 may be rotatable around the first link driving axis $BX_1$, and the second link 113 may be rotatable around the second link driving axis $BX_2$.

Rotation axes of the respective link driving units 200, and more specifically, the first link driving axis $BX_1$ and the second link driving axis $BX_2$, which are respectively at the ends of the link members 110, may intersect each other at one point. The target H may be positioned at the intersection point, and the collimator 300 may radiate the light L to the target H.

Referring to FIGS. 1 and 12, the collimator 300 may be coupled to an end of the link unit 100 and may contactlessly aim at the target H. The light L, e.g., radiation, may pass through the radiation area A formed in the collimator 300 and reach to the target H.

The structures, operating principles, and effects of the collimator 300 have been described above. Thus, redundant descriptions will be omitted.

According to an embodiment, a radiation area of light may be set using first and second moving members, so that the structure of a collimator may be simplified.

In addition, since the first moving member is rotatably installed in a base unit, the radiation area may become more various and directivity to a target may be increased, as compared to when the first moving member is linearly moved.

Moreover, as compared to the case when the first moving member is linearly moved, when the first moving member is rotatably installed in the base unit, the size of the collimator may be reduced by a distance along which the first moving member is linearly moved.

In addition, the first and second moving members may be independently actuated, and thus, it may be easy to control the collimator.

In addition, collision between link members may be prevented.

In addition, the target may be quickly and precisely aimed at, so that a treatment or surgical time may be reduced.

It should be understood that the embodiments described herein should be considered in a descriptive sense only and not for purposes of limitation. Descriptions of the features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A collimator comprising:
   a base configured to form a radiation path of light;
   a pair of first moving members rotatably installed in the base;
   a pair of second moving members movably installed in the base; and
   an actuator configured to externally receive power and transmit the power to the first moving members and the second moving members,
   wherein a first space is formed between the first moving members, a second space is formed between the second moving members, and the light passes through a radiation area corresponding to an overlapping area of the first space and the second space,
   wherein the actuator comprises:
   a first actuator installed at an end of each of the first moving members and configured to rotate each of the first moving members around a rotation shaft; and
   a second actuator configured to move the second moving members in a direction crossing a rotation direction of the first moving members.

2. The collimator of claim 1, wherein
   the second actuator is installed at an end of each of the second moving members and configured to move each of the second moving members along a motion shaft.

3. The collimator of claim 2, wherein the second moving members face each other with the second space formed therebetween and are moved parallel along the motion shaft.

4. The collimator of claim 1, wherein the second moving members are rotatably installed in the base.

5. The collimator of claim 4, wherein the first moving members and the second moving members are each curved with a predetermined radius of curvature.

6. The collimator of claim 5, wherein the pair of first moving members and the pair of the second moving members are respectively positioned on concentric spheres.

7. The collimator of claim 4, wherein the actuator comprises:
   a first actuator installed at an end of each of the first moving members and configured to rotate each of the first moving members around a first rotation shaft; and
   a second actuator installed at an end of each of the second moving members and configured to rotate each of the second moving members around a second rotation shaft.

8. A medical robot comprising:
   a link unit comprising a plurality of link members;
   a link driver configured to rotate the link members; and
   a collimator coupled to an end of the link unit and configured to contactlessly aim at a target,
   wherein the collimator comprises:
   a base configured to form a radiation path of light;
   a pair of first moving members rotatably installed in the base;
   a pair of second moving members movably installed in the base; and
   an actuator configured to externally receive power and transmit the power to the first moving members and the second moving members,
   wherein the actuator comprises:
   a first actuator installed at an end of each of the first moving members and configured to rotate each of the first moving members around a rotation shaft; and
   a second actuator configured to move the second moving members in a direction crossing a rotation direction of the first moving members.

9. The medical robot of claim 8, wherein rotation axes of the link driver intersect each other at one point and are formed respectively at ends of the link members.

10. The medical robot of claim 9, wherein the link members comprise:
    a first link; and a second link connected to an end of the first link.

11. The medical robot of claim 9, wherein the first link and the second link have each an arc shape and are respectively positioned on concentric spheres of which a center is the intersection point.

12. The medical robot of claim 8, wherein
    the second actuator is installed at an end of each of the second moving members and configured to move each of the second moving members along a motion shaft.

13. The medical robot of claim 12, wherein the second moving members face each other with a second space formed therebetween and are moved parallel along the motion shaft.

14. The medical robot of claim 8, wherein
    the second actuator is installed at an end of each of the second moving members and configured to rotate each of the second moving members around a second rotation shaft.

* * * * *